United States Patent
Harichian et al.

(10) Patent No.: US 7,468,464 B2
(45) Date of Patent: Dec. 23, 2008

(54) RESORCINOL DERIVATIVES FOR SKIN

(75) Inventors: Bijan Harichian, Brookfield, CT (US); Jose Guillermo Rosa, Shelton, CT (US)

(73) Assignee: Unilever Home & Personal Care USA, division of Conopco, Inc., Greenwich, CT (US)

(*) Notice: Subject to any disclaimer, the term of this patent is extended or adjusted under 35 U.S.C. 154(b) by 0 days.

(21) Appl. No.: 12/026,933

(22) Filed: Feb. 6, 2008

(65) Prior Publication Data

US 2008/0131382 A1 Jun. 5, 2008

Related U.S. Application Data

(63) Continuation of application No. 11/084,601, filed on Mar. 18, 2005.

(51) Int. Cl.
C07C 39/04 (2006.01)
C07C 39/23 (2006.01)
(52) U.S. Cl. .................. 568/716; 568/763
(58) Field of Classification Search .......... 568/716, 568/763
See application file for complete search history.

(56) References Cited

U.S. PATENT DOCUMENTS

| | | | |
|---|---|---|---|
| 2,589,205 A * | 3/1952 | Pohland | 546/236 |
| 4,129,413 A | 12/1978 | Rose et al. | |
| 4,959,393 A | 9/1990 | Torihara et al. | |
| 5,468,472 A | 11/1995 | LaGrange et al. | |
| 5,744,653 A | 4/1998 | Ito et al. | |
| 5,880,314 A | 3/1999 | Shinomiya et al. | |
| 6,132,740 A | 10/2000 | Hu | |
| 6,504,037 B2 | 1/2003 | Bradley et al. | |
| 6,828,460 B2 | 12/2004 | Collington et al. | |
| 6,852,310 B2 | 2/2005 | Harichian et al. | |
| 2004/0077654 A1 | 4/2004 | Bouillot et al. | |
| 2004/0235963 A1 | 11/2004 | Gattrell | |

FOREIGN PATENT DOCUMENTS

| | | |
|---|---|---|
| DE | 201 10 356 | 10/2001 |
| EP | 0 623 339 | 4/1994 |
| EP | 1 134 207 | 3/2001 |
| GB | 1 024 335 | 12/1964 |
| GB | 1581428 | 12/1980 |
| JP | 04 159511 | 6/1992 |
| JP | 06 056641 | 3/1994 |
| JP | 11-255638 | 9/1999 |
| JP | 11-255639 | 9/1999 |
| JP | 2000-327557 | 11/2000 |
| JP | 2001-010925 | 1/2001 |
| WO | 99/55680 | 11/1999 |
| WO | 02/055496 | 7/2002 |
| WO | 03/080009 | 10/2003 |
| WO | 2004/092123 | 10/2004 |

OTHER PUBLICATIONS

International Search Report on Application No. PCT/EP2006/001099 dated Jul. 11, 2006.

(Continued)

*Primary Examiner*—Elvis O Price
(74) *Attorney, Agent, or Firm*—Edward A. Squillante, Jr.; Ellen Plotkin

(57) ABSTRACT

New 4-substituted resorcinol derivatives of general formula I and/or B and process for synthesizing same, cosmetic compositions and methods of using same, particularly for skin lightening:

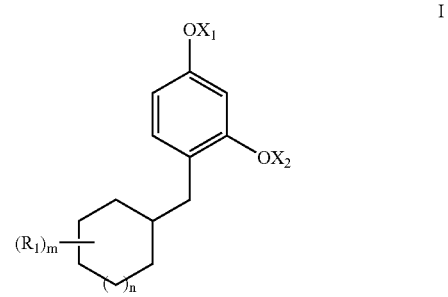

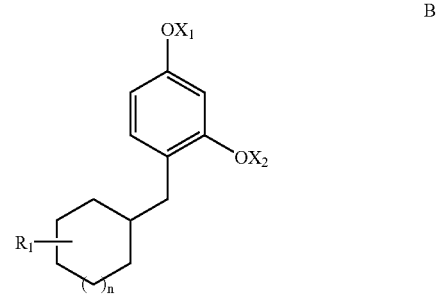

Wherein
$X_1$ and/or $X_2$ represents hydrogen (H), linear or branched, saturated or unsaturated $C_1$-$C_{12}$ alkyl, alkenyl, or acyl groups. Preferably, $X_1$ and/or $X_2$ represents hydrogen (H); linear or branched, saturated or unsaturated $C_1$-$C_{12}$ alkyl or acyl groups;
$R_1$ represents hydrogen (H), linear or branched, cyclic or acyclic, saturated or unsaturated $C_1$-$C_{12}$ alkyl, alkenyl, cycloalkyl, or cycloalkenyl group. Preferably, $R_1$ represents hydrogen (H) or a $C_1$ alkyl group (i.e, methyl group). More preferably, $R_1$ represents hydrogen;
n represents 0, 1. When n=0, the ring is a cyclopentyl with or without one heteroatom from O, N or S and/or with or without one double bond. When n=1, the ring is a cyclohexyl with or without one heteroatom from O, N or S and/or with or without one double bond; and
m represents an integer between 1 and 6.

7 Claims, No Drawings

OTHER PUBLICATIONS

Talbot et al., J. Amer. Chem. Soc., 49, 1927. pp. 2040-2042., Abstract only.

Database Capius, Chemical Abstracts Service. "*alpha-Halogenated amines, XIX. Aminomethylation of phenolethers*", XP002384915, 1967.

Database Caplus, Chemical Abstracts Service. "*Pharmacological investigation of synthetic substances substances showing oxylocic action; substituted Npbenzylpiperdeines and 3, 4-dimethoxybenzylamines*", XP002384916. 1959.

Database Caplus, Chemical Abstracts Service, "*Synthesis uterofonics. I. Substituted 1-benzylpiperidines*", XP002384917, 1953.

Ohtaka et al., "*Benzylpiperazine Derivatives. VII. II Studies on the role of the nitrogen atom in the cerebral vasodlating activity of 1-benzyl-4-diphenyl-methylpiperazine derivatives*", chemical and Pharmaceutical society of Japan, Vo. 35, No. 1, pp. 4637-4641, 1982.

Database Beilstein, XP-002384918, Database accesion No. 3282817, 3268138, 3265793, 3254680 (BRN) & J. Am. Chem., Soc., vol. 75, 1953. pp. 2341-2342.

Database Chemicals, Chemical Abstracts Service, XP002384919, Order Nos. 5458833, 542863.

"The Properties and Chemistry of Resorcinol", Chapter 2, pp. 5-25.

Burtner, Robert R., J. Amer. Chem. Soc., 75, 1953, pp. 2341-2344.

\* cited by examiner

RESORCINOL DERIVATIVES FOR SKIN

This application is a continuation of Ser. No. 11/084,601, filed Mar. 18, 2005, now pending.

FIELD OF THE INVENTION

The invention relates to 4-substituted cyclo-alkyl methyl resorcinol derivatives, cosmetic compositions containing same, and cosmetic methods of using and making same. More specifically, the present invention relates to 4-substituted cyclo-alkyl methyl resorcinol derivatives as skin lightening actives, cosmetic compositions and methods of using same for skin lightening.

BACKGROUND OF THE INVENTION

Many people are concerned with the degree of pigmentation of their skin. For example, people with age spots or freckles may wish such pigmented spots to be less pronounced. Others may wish to reduce the skin darkening caused by exposure to sunlight or to lighten their natural skin color. To meet this need, many attempts have been made to develop products that reduce the pigment production in the melanocytes. However, the substances identified thus far tend to have either low efficacy or undesirable side effects, such as, for example, toxicity or skin irritation. Therefore, there is a continuing need for new skin lightening agents, with improved overall effectiveness, as well as agents that lend themselves to ease of processing in their manufacture.

Resorcinol derivatives are generally known compounds and can be readily obtained, for example, by a method wherein a saturated carboxylic acid and resorcinol are condensed in the presence of zinc chloride and the resultant condensate is reduced with zinc amalgam/hydrochloric acid (Lille. J. Bitter, L A. Peiner. V, Tr. Nauch-Issled. Inst. slantsev 1969, No. 18, 127), or by a method wherein resorcinol and a corresponding alkyl alcohol are reacted in the presence of an alumina catalyst at a high temperature of from 200 to 400° C. (British Patent No. 1,581,428).

Resorcinol derivatives have cosmetic skin and hair benefits. Certain resorcinol derivatives, particularly 4-substituted resorcinol derivatives, are useful in cosmetic compositions for skin lightening benefits. Resorcinol derivatives are described in many publications, including U.S. Pat. No. 4,959,393; Hu et al., U.S. Pat. No. 6,132,740; Bradley, et al., U.S. Pat. No. 6,504,037; and Japanese published patent applications JP 2001-010925 and JP2000-327557. Skin lightening compounds that may be derived from coumarin are disclosed in U.S. Patent Publication No. 2004/0042983. Some of these compounds can be difficult to formulate and/or irritating to the skin.

Applicants have now discovered new compounds that which deliver skin lightening benefits. The general chemical formulas and structures of these compounds are discussed in more detail herein below. Especially, 4-substituted cycloalkyl methyl resorcinol derivatives, have been found to be effective and possibly less irritating to the skin and are relatively simple to manufacture.

SUMMARY OF THE INVENTION

Applicants have now discovered new 4-substituted resorcinol derivatives that have skin lightening activity. Accordingly, the present invention provides novel compounds of general formula I, of which compound of general formula B is an example, cosmetic compositions and methods comprising same, particularly for skin lightening, as well as a process for producing the inventive compounds:

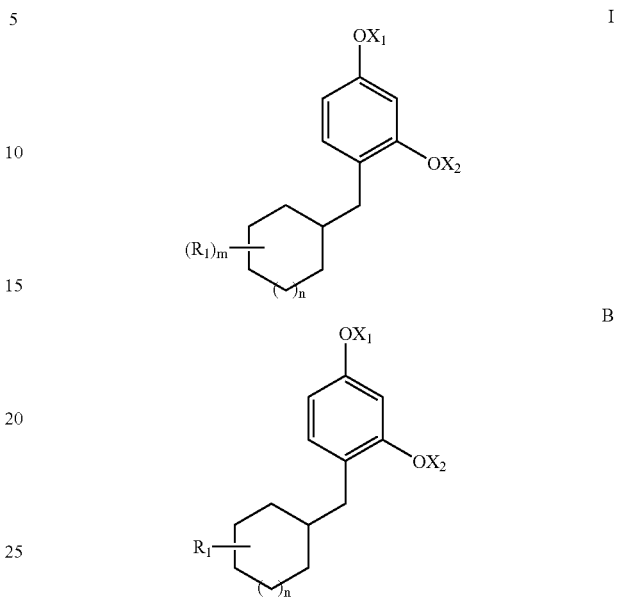

Wherein $X_1$ and/or $X_2$ represents hydrogen (H), linear or branched, saturated or unsaturated $C_1$-$C_{12}$ alkyl, alkenyl, acyl groups. Preferably, $X_1$ and/or $X_2$ represents hydrogen (H); linear or branched, saturated or unsaturated $C_1$-$C_{12}$ alkyl or acyl groups. More preferably, $X_1$ and/or $X_2$ represents hydrogen.

$R_1$ represents hydrogen (H), linear or branched, cyclic or acyclic, saturated or unsaturated $C_1$-$C_{12}$ alkyl, alkenyl, cycloalkyl, or cycloalkenyl group. Preferably, $R_1$ represents hydrogen (H) or $C_1$ alkyl group (i.e, methyl group). More preferably, $R_1$ represents hydrogen.

n represents 0, 1. When n=0, the ring is a cyclopentyl with or without one heteroatom from O, N or S and/or with or without one double bond. When n=1, the ring is a cyclohexyl with or without one heteroatom from O, N or S and/or with or without one double bond.

m=1, 2, 3, 4, 5, 6 (i.e, an integer between 1 and 6).

Preferred compounds include:

n=0, m=1, $R_1$=H, alkyl, and/or alkenyl; anywhere in the ring.

n=1, m=1, $R_1$=H, alkyl, and/or alkenyl; anywhere in the ring.

n=0, m=2-5, $R_1$=H, alkyl, and/or alkenyl; any substitution pattern anywhere in the ring.

n=1, m=2-6, $R_1$=H, alkyl and/or alkenyl; any substitution pattern anywhere in the ring.

Cosmetic compositions according to the present invention include:

a. about 0.0001 wt. % to about 50 wt. % of a 4-substituted resorcinol derivative of the general formula B; and b. a cosmetically acceptable vehicle.

The inventive compounds and compositions may be applied to the skin as part of inventive cosmetic method for skin lightening.

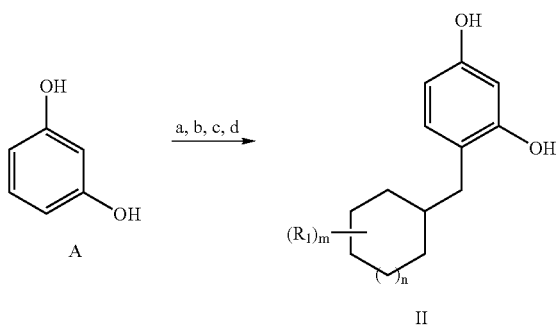

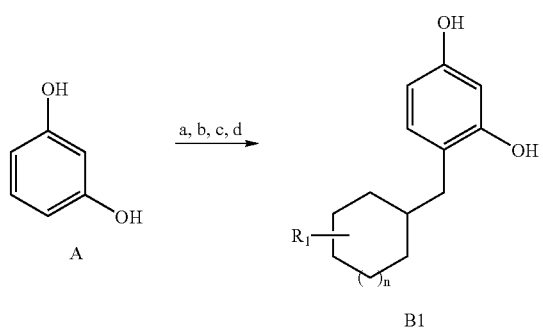

In another aspect, the present invention relates to a process for synthesizing the novel resorcinol compounds of general formula I, II and/or B1, having the following general reaction scheme:

Wherein a, b, c, d represent reaction steps, reagents and conditions:
(a) cycloalkylcarbonyl chloride, $ZnCl_2$, organic solvent (e.g. dichloromethane); (b) acetic anhydride, triethylamine; (c) hydrogen, catalyst (e.g. Pd/C), acid (e.g. acetic); (d) aqueous acid hydrolysis (e.g. 3M HCl:methanol).

DETAILED DESCRIPTION OF THE INVENTION

The invention is concerned with new 4-substituted resorcinol derivatives for cosmetically lightening skin color, cosmetic compositions and methods emplying same, and a process for producing same.

As used herein, the term "cosmetic composition" is intended to describe compositions for topical application to human skin, including leave-on and wash-off products.

The term "skin" as used herein includes the skin on the face, neck, chest, back, arms, axillae, hands, legs, and scalp.

Except in the examples, or where otherwise explicitly indicated, all numbers in this description indicating amounts of material or conditions of reaction, physical properties of materials and/or use are to be understood as modified by the word "about". All amounts are by weight of the composition, unless otherwise specified.

For the avoidance of doubt, the term "comprising" means including, made up of, composed of, consisting and/or consisting essentially of. Furthermore, in the ordinary meaning of "comprising," the term is defined as not being exhaustive of the steps, components, ingredients, or features to which it refers.

4-Substituted Cyclo-Alkyl Methyl Resorcinol Derivatives

The present invention is based on a new resorcinol derivative of the general formula I, of which compounds of general formula B are preferred:

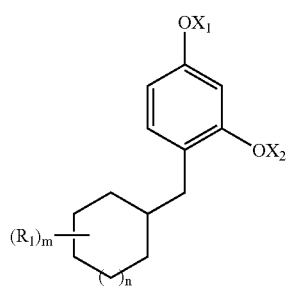

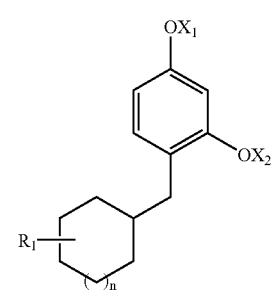

Wherein $X_1$ and/or $X_2$ represents hydrogen (H), linear or branched, saturated or unsaturated $C_1$-$C_{12}$ alkyl, alkenyl, or acyl groups. Preferably, $X_1$ and/or $X_2$ represents hydrogen (H); linear or branched, saturated or unsaturated $C_1$-$C_{12}$ alkyl or acyl groups.

$R_1$=hydrogen (H), linear or branched, cyclic or acyclic, saturated or unsaturated $C_1$-$C_{12}$ alkyl, alkenyl, cycloalkyl, or cycloalkenyl group. Preferably, $R_1$ represents hydrogen (H) or a $C_1$ alkyl group (i.e, methyl group). More preferably, $R_1$ represents hydrogen.

n represents 0, 1. When n=0, the ring is a cyclopentyl with or without one heteroatom from O, N or S and/or with or without one double bond. When n=1, the ring is a cyclohexyl with or without one heteroatom from O, N or S and/or with or without one double bond.

m=1, 2, 3, 4, 5, 6 (i.e, an integer between 1 and 6).

Preferred compounds include:

n=0, m=1, $R_1$=H, alkyl, or alkenyl; anywhere in the ring.

n=1, m=1, $R_1$=H, alkyl and/or alkenyl; anywhere in the ring.

n=0, m=2-5, $R_1$=H, alkyl and/or alkenyl; any substitution pattern anywhere in the ring.

n=1, m=2-6, $R_1$=H, alkyl and/or alkenyl; any substitution pattern anywhere in the ring.

Examples of more specific embodiments of the 4-substituted cycloalkyl-methyl resorcinols include compounds of general formula B1:

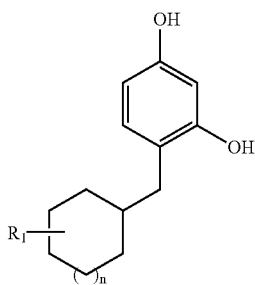

B1

Wherein $R_1$=hydrogen (H), linear or branched, cyclic or acyclic, saturated or unsaturated $C_1$-$C_{12}$ alkyl, alkenyl, cycloalkyl, or cycloalkenyl group. Preferably, $R_1$ represents hydrogen (H) or a $C_1$ alkyl group (i.e, methyl group). More preferably, $R_1$ represents hydrogen.

n represents 0, 1. When n=0, the ring is a cyclopentyl with or without one heteroatom from O, N or S and/or with or without one double bond. When n=1, the ring is a cyclohexyl with or without one heteroatom from O, N or S and/or with or without one double bond.

Preferred compounds are 4-cyclopentyl methyl resorcinol, 4-cyclohexyl methyl resorcinol.

Cosmetic compositions according to the present invention include:

a. about 0.0001 wt. % to about 50 wt. % of a 4-substituted resorcinol derivative of the general formula B; and b. a cosmetically acceptable vehicle.

The amount of the resorcinol derivative is preferably in the range of about 0.00001% to about 10%, more preferably about 0.001 to 7%, most preferably from 0.01% to about 5%, of the total amount of a cosmetic composition.

The inventive compounds and compositions may be applied to the skin as part of inventive cosmetic method for skin lightening.

Synthetic Process for Novel Resorcinol Derivatives

I. General Reaction Scheme[a]

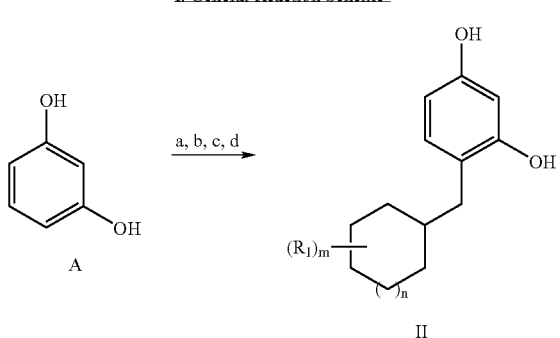

Wherein a, b, c, d represent reaction steps, reagents and conditions: (a) cycloalkylcarbonyl chloride, $ZnCl_2$, organic solvent (e.g. dichloromethane, chloroform); (b) acetic anhydride, triethylamine; (c) hydrogen, catalyst (e.g. Pd/C), acid (e.g. acetic); (d) aqueous acid hydrolysis (e.g. 3M HCl: methanol).

II. General Procedure a. A cycloalkylcarbonyl derivative (e.g. cyclohexylcarbonyl when n represents 1) or substituted cycloalkyl carbonyl derivative (e.g. mono-substituted when m represents 1, or multisubstituted when m represents an integer greater than 1) is added to a suspension of zinc chloride in an organic solvent (i.e. dichloromethane, chloroform), followed by resorcinol A and the reaction vigorously stirred at or above 25° C. (i.e. 25 to 100° C.) and monitored using a suitable analytical method (i.e. TLC, GC, LC) until complete consumption of the starting material. The reaction is diluted with an organic solvent and washed successively with aqueous acid (i.e 1N HCl) and aqueous base (i.e. saturated $NaHCO_3$). The solvents are removed under reduced pressure and the product is purified using conventional methods (i.e. recrystallization, distillation, chromatography) to give a cycloalkylcarbonyl resorcinol derivative.

b. The cycloalkylcarbonyl resorcinol derivative is dissolved in a mixture of acetic anhydride and triethylamine and the reaction is monitored using a suitable analytical method (i.e. TLC, GC, LC) until complete consumption of the starting material. The solvents are removed under reduced pressure and the product is purified using conventional methods (i.e. recrystallization, distillation, chromatography) to give cycloalkylcarbonyl resorcinol diacetate.

c. A high pressure reaction vessel is charged with the cycloalkylcarbonyl resorcinol diacetate in acetic acid and a catalyst is added (i.e. homogeneous or heterogeneous catalysts such as Pd attached to a suitable matrix). The reactor is pressurized with hydrogen (i.e. 100 to 800 psi) and stirred above 25° C. (i.e. 25 to 60° C.) until complete consumption of the reactant is observed as monitored using a suitable analytical method (i.e. TLC, GC, LC, hydrogen consumption). The reaction mixture is filtered through an insoluble support (i.e. celite, silica gel), the solvents removed under reduced pressure and the product purified using conventional methods (i.e. recrystallization, distillation, chromatography) to give cycloalkylmethyl resorcinol monoacetate.

d. The cycloalkylmethyl resorcinol monoacetate is dissolved in aqueous acidic media (i.e. aqueous acetic acid) and stirred at or above 23° C. (i.e. 23 to 150° C.) until complete consumption of the reactant is observed as monitored using a suitable analytical method (i.e. TLC, GC, LC). The solvents are removed under reduced pressure and the product is purified using conventional methods (i.e. recrystallization, distillation, chromatography) to give cycloalkylmethyl resorcinol of general formula II.

Skin Benefit Agents

Preferred cosmetic compositions are those suitable for the application to human skin, which optionally, but preferably, include a skin benefit agent.

Suitable skin benefit agents include anti-aging, wrinkle-reducing, skin whitening, anti-acne, and sebum reduction agents. Examples of these include alpha-hydroxy acids and esters, beta-hydroxy acids and esters, polyhydroxy acids and esters, kojic acid and esters, ferulic acid and ferulate derivatives, vanillic acid and esters, dioic acids (such as sebacic and azoleic acids) and esters, retinol, retinal, retinyl esters, hydroquinone, t-butyl hydroquinone, mulberry extract, licorice extract, and resorcinol derivatives other than the 4-substituted resorcinol derivatives discussed hereinabove.

Cosmetically Acceptable Carrier

The skin benefit agent together with the organic sunscreen compound and resorcinol derivative of the invention is usually used along with a cosmetic base. Suitable cosmetic carriers are well known to one skilled in the art. The cosmetic bases may be any bases which are ordinarily used for skin benefit agents and are not thus critical. Specific preparations of the cosmetics to which the skin benefit agents of the invention is applicable include creams, ointments, emulsions, lotions, oils, packs and nonwoven wipes. Cream bases are, for example, beeswax, cetyl alcohol, stearic acid, glycerine, propylene glycol, propylene glycol monostearate, polyoxyethylene cetyl ether and the like. Lotion bases include, for example, oleyl alcohol, ethanol, propylene glycol, glycerine, lauryl ether, sorbitan monolaurate and the like.

The cosmetically acceptable vehicle may act as a dilutant, dispersant or carrier for the skin benefit ingredients in the composition, so as to facilitate their distribution when the composition is applied to the skin.

The vehicle may be aqueous, anhydrous or an emulsion. Preferably, the compositions are aqueous or an emulsion, especially water-in-oil or oil-in-water emulsion, preferentially oil in water emulsion. Water when present will be in amounts which may range from 5 to 99%, preferably from 20 to 70%, optimally between 40 and 70% by weight.

Besides water, relatively volatile solvents may also serve as carriers within compositions of the present invention. Most preferred are monohydric $C_1$-$C_3$ alkanols. These include ethyl alcohol, methyl alcohol and isopropyl alcohol. The amount of monohydric alkanol may range from 1 to 70%, preferably from 10 to 50%, optimally between 15 to 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably is chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate and arachidyl behenate.
(5) Sterol esters, of which cholesterol fatty acid esters are examples.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as cosmetically acceptable carriers in compositions of this invention. The humectant aids in increasing the effectiveness of the emollient, reduces skin dryness and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. For leave-on products, total concentration of the surfactant will range from 0.1 to 40%, preferably from 1 to 20%, optimally from 1 to 5% by weight of the composition. For wash-off products, such as cleansers and soap, total concentration of surfactant will range at about 1 to about 90%. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, acyl glutamates, $C_8$-$C_{20}$ alkyl ether phosphates and combinations thereof.

The inventive cosmetic compositions optionally contain a lathering surfactant. By a "lathering surfactant" is meant a surfactant which, when combined with water and mechanically agitated, generates a foam or lather. Preferably, the lathering surfactant should be mild, meaning that it must provide sufficient cleansing or detergent benefits but not overly dry the skin, and yet meet the lathering criteria described above. The cosmetic compositions of the present invention may contain a lathering surfactant in a concentration of about 0.01% to about 50%.

Optional Components

In the cosmetic compositions of the invention, there may be added various other plasticizers, elastomers, calamine, pigments, antioxidants, chelating agents, and perfumes, as well as organic sunscreens and sunscreens such UV diffusing agents, typical of which is finely divided titanium oxide and zinc oxide.

Other adjunct minor components may also be incorporated into the cosmetic compositions. These ingredients may include coloring agents, opacifiers, and perfumes. Amounts of these other adjunct minor components may range anywhere from 0.001% up to 20% by weight of the composition.

Organic Sunscreens

The inventive cosmetic compositions include an organic sunscreen to provide protection from the harmful effects of excessive exposure to sunlight. Organic sunscreens for purposes of the inventive compositions are organic sunscreen agents having at least one chromophoric group absorbing within the ultraviolet range of from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl)ether; Hydroquinone; Benzophenones (Oxybenzone, Sulisobenzone, Dioxybenzone, Benzoresorcinol, 2,2', 4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-dibenzoylmethane).

Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid and mixtures thereof.

Suitable commercially available organic sunscreen agents are those identified under the following table.

TABLE 1

| CTFA Name | Trade Name | Supplier |
|---|---|---|
| Benzophenone-3 | UVINUL M-40 | BASF Chemical Co. |
| Benzophenone-4 | UVINUL MS-40 | BASF Chemical Co. |
| Benzophenone-8 DEA | SPECRA-SORB UV-24 | American Cyanamide |
| Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KEMESTER HMS | Hunko Chemical |
| Methyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Bernel Chemical |
| Octyl salicylate | SUNAROME WMO | Felton Worldwide |
| PABA | PABA | National Starch |
| 2-Phenylbenzimidazole-5-sulphonic acid | EUSOLEX 232 | EM Industries |
| TEA salicylate | SUNAROME W | Felton Worldwide |
| 3-(4-methylbenzylidene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl methoxy dibenzoyl methane | PARSOL 1789 | Givaudan Corp. |
| Etocrylene | UVINUL N-35 | BASF Chemical Co. |

The amount of the organic sunscreens in the personal care composition is generally in the range of about 0.01% to about 20%, preferably in the range of about 0.1% to about 10%.

Preferred organic sunscreens are PARSOL MCX and Parsol 1789, due to their effectiveness and commercial availability.

Use of the Composition

The composition according to the invention is intended primarily as a cosmetic product for topical application to human skin, preferably for cosmetic skin lightening.

In use, a small quantity of the composition, for example about 0.1 to about 5 ml, is applied to exposed areas of the skin, from a suitable container or applicator and, if necessary, it is then spread over and/or rubbed into the skin using the hand or fingers or a suitable device.

Product Form and Packaging

The cosmetic composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto.

EXAMPLES 1-7

A set of compositions within the scope of the present invention were prepared and listed in the Table below. The compositions are in weight percent.

TABLE 2

| Ingredient Trade and CTFA Name | Phase | 1 | 2 | 3 | 4 | 5 | 6 | 7 |
|---|---|---|---|---|---|---|---|---|
| Stearic acid | A | 14.9 | 14.9 | 12.9 | 17.9 | 14.0 | 14.0 | 14.0 |
| Sodium cetearyl sulfate | A | 1.0 | 1.0 | 1.5 | 1.5 | 1 | 1 | 1 |
| Myrj 59 | A | 2.0 | 1.5 | 2 | 2 | 2 | 2 | 2 |
| Span 60 | A | 2.0 | 1.5 | 2 | 2 | 2 | 2 | 2 |
| Propyl paraben | A | 0.10 | 0.10 | 0.10 | 0.10 | 0.10 | 0.10 | 0.10 |
| BHT | A | 0.1 | 0.1 | 0.1 | 0.1 | 0.1 | 0.1 | 0.1 |
| Dimethicone | A |  | 0.50 | 0.75 |  | 0.75 | 0.75 | 0.75 |
| Water | B | BAL* | BAL | BAL | BAL | BAL | BAL | BAL |
| EDTA | B | 0.04 | 0.04 | 0.04 | 0.04 | 0.04 | 0.04 | 0.04 |
| Pemulen TR 2 | B |  | 0.10 | 0.05 |  | 0.05 | 0.05 | 0.05 |
| Methyl paraben | B | 0.15 | 0.15 | 0.15 | 0.15 | 0.15 | 0.15 | 0.15 |
| Parsol MCX (organic sunscreen) | C | 0.75 | 1.25 | 1 | 1 | 0.75 | 0.75 | 0.75 |
| Parsol 1789 (organic sunscreen) | C | 0.40 |  | 0.4 | 0.4 | 0.4 | 0.4 | 0.4 |
| Micronized Titanium oxide | C |  |  |  |  | 0.2 | 0.2 | 0.2 |
| Propylene glycol | D |  |  |  |  | 8 | 8 | 8 |
| Transcutol | D |  |  |  |  | 4 | 4 | 4 |
| 4-cyclopentyl methyl resorcinol | D | 0.05 | 2.0 | 2.0 | 3.5 |  |  |  |
| 4-cyclohexyl methyl resorcinol | D |  |  |  |  | 2.5 |  |  |
| 4-cyclothiane methyl resorcinol | D |  |  |  |  |  | 3.51 |  |
| 4-cycloamido methyl resorcinol | D |  |  |  |  |  |  | 5.0 |

*BAL = balanced to 100%

The compositions of Examples 1-7 in the Table above were prepared in the following fashion. Phase A is heated at 75° C. Phase B is heated to 75° C. in a container separate from that of Phase A. Thereafter the phases are combined with mixing with heat being turned off. Phase C was premixed and warmed then added immediately after phase A and B mixed. Phase D is pre-dissolved and added into the main pot at 60° C. The mixture is cooled until 40° C. and then packed.

EXAMPLE 8

This Example demonstrate an inventive process for producing 4-cyclohexyl methyl resorcinol (CHMR).

General Reaction Scheme[a]

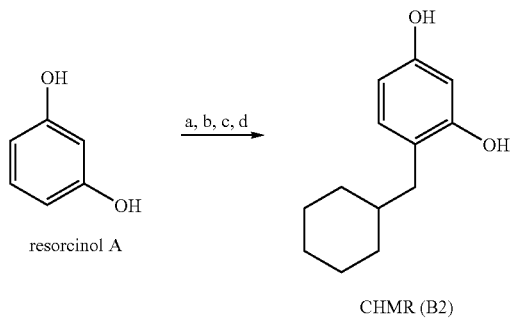

resorcinol A

CHMR (B2)

[a]Reagents and conditions: (a) cyclohexylcarbonyl chloride, $ZnCl_2$, dichloromethane, 64 h at R.T. (room temperature of about 20-25° C.); (b) acetic anhydride, triethylamine, tetrahydrofuran, 4 h at R.T.; (c) hydrogen, 5% Pd/C, acetic acid, 16 h at 30° C., 16 h at 50° C.; (d) 3M HCl:methanol (16:84), 4 h at R.T.

Detailed Reaction Scheme[a]

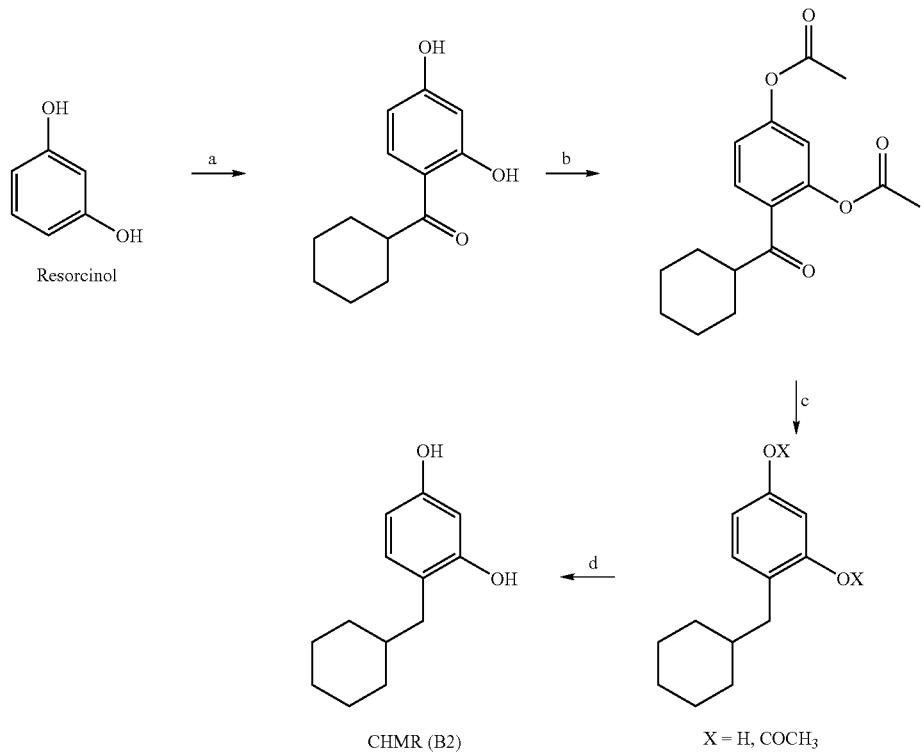

CHMR (B2)

X = H, COCH$_3$

[a]Reagents and conditions: (a) cyclohexylcarbonyl chloride, ZnCl$_2$, dichloromethane, 64 h at R.T.; (b) acetic anhydride, triethylamine, tetrahydrofuran, 4 h at R.T.; (c) hydrogen, 5% Pd/C, acetic acid, 16 h at 30° C., 16 h at 50° C.; (d) 3M HCl:methanol (16:84), 4 h at R.T.

Specific Procedure: 4-cyclohexyl methyl resorcinol (CHMR or B2)

Cyclohexylcarbonyl chloride (1.54 ml, 11.3 mmol) was added to a suspension of zinc chloride (4.20 g, 31.4 mmol) in dichloromethane (10 ml) at room temperature, followed by resorcinol A (1.38 g, 12.5 mmol) and the solution stirred for 3 h (Note 1). At this time, TLC showed the formation of a major product ($R_f$ 0.45) and resorcinol ($R_f$ 0.10) (Note 2). After a total of 64 h, the mixture was partitioned between ethyl ether (200 ml) and 1 M HCl (50 ml), washed sequentially with 1 M HCl (2×25 ml), saturated NaHCO$_3$ (2×25 ml), saturated NaCl (50 ml), dried (Na$_2$SO$_4$), filtered and the solvent removed to give a yellow oil (2.75 g) (Note 3). The crude product was purified by flash chromatography to give 4-cyclohexylcarbonyl resorcinol (1.5 g, 88% purity) (Note 4).

Acetic anhydride (1.58 ml, 16.7 mmol) was added to a solution of 4-cyclohexylcarbonyl resorcinol (1.47 g, 6.68 mmol) in tetrahydrofuran (15 ml) at room temperature, followed by triethylamine (2.80 ml, 20.0 mmol) and the solution stirred for 4 h. At this time, TLC showed the clean formation of a single product ($R_f$ 0.71) and no starting material ($R_f$ 0.40) (Note 5). The solvent was removed under reduced pressure to give 4-cyclohexylcarbonyl resorcinol diacetate as a light-yellow oil (3.0 g) and used without further purification for the next synthetic step (Note 6).

A Parr hydrogenator (1 L) was charged with crude 4-cyclohexylcarbonyl resorcinol diacetate (3.0 g, 60% purity, 5.9 mmol) and acetic acid (50 ml) under nitrogen (Note 7). A suspension of 5% Pd/C (200 mg, Engelhard) in acetic acid (50 ml) was added and the reactor sealed, evacuated and purged with nitrogen (4×). The reactor was pressurized to 100 psi with hydrogen and stirred at 30° C. for 16 h, 50° C. for 16 h, recharged with catalyst (250 mg), pressurized to 200 psi H$_2$ and stirred at 50° C. for 16 h, and finally recharged with catalyst (400 mg), pressurized to 200 psi H$_2$ and stirred at 50° C. for 64 h (Note 8). At this time, GC showed the formation of products at the expense of starting material (Note 9). The reactor was evacuated, purged with nitrogen and the mixture filtered through celite (Note 10). The solvent was removed to give 4-cyclohexylmethyl resorcinol monoacetate as a light amber-colored oil which crystallized upon standing at room temperature (2.76 g).

3 M HCl (13 ml) was added to a solution of crude 4-cyclohexylmethyl resorcinol monoacetate (2.71 g) in methanol (70 ml) and the solution stirred at room temperature for 16 h. At this time, TLC showed the clean formation of product ($R_f$ 0.14) and traces of starting material ($R_f$ 0.48) (Note 11). The solvent was reduced to ⅓ volume under reduced pressure and partitioned between ethyl ether (300 ml) and 1 M HCl (100 ml), washed with saturated NaCl (100 ml), the aqueous layer back extracted with ethyl ether (200 ml), the organic layers dried (Na$_2$SO$_4$), filtered and the solvent removed to give 4-cyclohexyl methyl resorcinol as a light amber-colored oil which crystallized upon standing at room temperature (1.1 g, 75% yield). The crude product was purified by flash chromatography to give 4-cyclohexyl methyl resorcinol B2 as a white solid (617 mg, 51% yield) (Note 12): m.p. 112-113° C.; $^1$H NMR (60 MHz, acetone-d$_6$) delta 1.08-1.76 (m, 11H), 2.44 (d, JJ=6.2 Hz, 2H), 6.26 (dd, JJ=7.9, 2.3 Hz, 1H), 6.39 (m, 1H), 6.86 (d, JJ=7.9 Hz, 1H), 7.90 (s, 1H); $^{13}$C NMR (60 MHz, acetone-d$_6$) delta 27.3, 33.3, 38.2, 39.5, 102.9, 106.7, 119.0, 132.5, 157.0, 157.4; m/z (EI; TMS derivatized; M$^+$) 350.

Notes
1. During the first five minutes of the reaction a gas is given off and pressure needs to be released.
2. The reaction was monitored using thin layer chromatography (TLC) by partitioning a reaction aliquot (10 uL) into diethyl ether:1M HCl (300 uL:300 uL), spotting the organic layer into a silica gel plate, eluting with 5% methanol in chloroform, and visualizing with UV and PMA stain. Alternately, the organic layer can be analyzed by gas chromatography (GC).
3. Analysis by GC and GC-MS showed 70% cyclohexylcarbonyl resorcinol (C-acylated resorcinol), 17% resorcinol, 7% cyclohexylcarbonyl resorcinol monoester (O-acylated resorcinol) and 5% unknown.
4. Flash chromatography was performed using silica gel as the stationary phase and 4% methanol in chloroform as the eluent.
5. The reaction was monitored using thin layer chromatography (TLC) by partitioning a reaction aliquot (30 uL) into diethyl ether:1M HCl (300 uL:300 uL), spotting the organic layer into a silica gel plate, eluting with 4% methanol in chloroform, and visualizing with UV and PMA stain. Alternately, the organic layer can be analyzed by gas chromatography (GC).
6. Based on weight %, GC and GC-MS analysis, the crude material is comprised of 4-cyclohexylcarbonyl resorcinol diacetate (60%), 1-acetoxy-3-cyclohexanecarbonyloxybenzene (6%) and acetic anhydride (34%).
7. The purity of 4-cyclohexylcarbonyl resorcinol diacetate does not have to be 100% for this reaction to work properly. In addition, the reagent concentration can be increased without affecting reaction quality.
8. The amount of catalyst, hydrogen pressure, temperature and reaction time can be varied. In this case, a reaction intermediate arising from hydrogenation of the starting material was stable at 30° C. and 100 psi H$_2$ and the conditions were modified (i.e. additional amounts of catalyst added, higher pressures and temperatures) to convert this intermediate to the final desired product.
9. Analysis by GC and GC-MS showed 4-cyclohexylmethyl resorcinol monoacetate as the major product (85%) and several minor products (15%). The reaction was monitored by filtering a reaction aliquot (1 mL) through glass wool, removal of the solvent under reduced pressure, derivatizing the crude residue to trimethylsilane (TMS) derivatives and analysis by GC and GC-MS.
10. If thermally-driven hydrolysis of this material is desired, this crude solution can be used directly for the next reaction by addition of 0.2 volumes of water and refluxing.
11. The reaction was monitored using TLC by partitioning a reaction aliquot (50 uL) into ethyl acetate:1M HCl (300 uL:300 uL), spotting the organic layer into a silica gel plate, eluting with 4% methanol in chloroform, and visualizing with UV and PMA stain. Alternately, the organic layer can be analyzed by gas chromatography (GC).
12. Flash chromatography was performed using silica gel as the stationary phase and 7% methanol in chloroform as the eluent.

EXAMPLE 9

This example demonstrates the skin lightening activity of 4-cycloalkyl methyl resorcinol.

Mushroom Tyrosinase Assay

Mushroom tyrosinase inhibition is indicative of reduction in melanin synthesis, thereby showing skin lightening effect.

Reagents:

Assay buffer: phosphate (100 mM, pH 7.0)

Mushroom tyrosinase stock solution (Sigma-Aldrich, Batch # 023K7024):
  0.2 mg/ml in assay buffer L-DOPA stock solution: 1.05 mM in assay buffer Test compound stock solutions: 10 mM in DMSO Assay Conditions:

Mushroom tyrosinase: 0.1 mg/ml in assay buffer

L-DOPA: 0.5 mM in assay buffer

Test compounds: various concentrations, 2.5% final [DMSO]

Temperature: room temperature

Procedure:
  Test compounds (5 uL of stock solutions) are added into wells of a 96-well plate, followed by L-DOPA (L-3,4-Dihydroxyphenylalanine; 95 uL of stock solution).

The reaction is started by adding mushroom tyrosinase (100 uL of stock solution) into each well and the absorbance is monitored at 490 nm over a time period of 30 sec to 2 min. The initial reaction velocity in the presence or absence of test compounds is calculated (Δ490 nm/min) and the % inhibition of test compounds is calculated using the following equation:

$$\% \text{ Inhibition} = \left(1 - \frac{v_i - v}{v_0 - v}\right) * 100$$

where $v_0$ is the initial reaction velocity in the absence of compound, v is the slope of the reaction in the absence of mushroom tyrosinase and $v_i$ is the slope of the reaction in the presence of test compound. The data (% inhibition vs. [test compound]) is fitted using data analysis software and the concentration of test compound at 50% inhibition (IC50) is determined from the fitted data.

TABLE 3

| Name | IC50 (uM) |
| --- | --- |
| 4-cyclohexylmethyl resorcinol (CHMR) | 0.95 |
| 4-ethyl resorcinol (ER) | 1.10 |

The IC50 value refers to the skin lightener concentration that results in 50% tyrosinase inhibition relative to the control (with a goal being obtaining maximum tyrosinase inhibition at minimum concentration).

The data appear to show that cyclohexyl methyl resorcinol and ethyl resorcinol have comparable potency.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic method of skin lightening comprising applying to the skin a composition comprising:
(a) a compound comprising the formula:

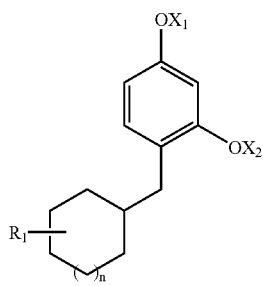

Wherein
X$_1$ and X$_2$ are independently represented as hydrogen (H), linear or branched, saturated or unsaturated C$_1$-C$_{12}$ alkyl, alkenyl, or acyl groups;
R$_1$=linear or branched, cyclic or acyclic, saturated or unsaturated C$_1$-C$_{12}$ alkyl, alkenyl, cycloalkyl, or cycloalkenyl group;
n=0,1; and
when n=0, the ring is cyclopentyl with or without one heteroatom from O, N or S and/or with or without one double bond; or
when n=1, the ring is cyclohexyl with or without one heteroatom from O, N or S and/or with or without one double bond and R$^1$ is not methyl; and
(b) a cosmetically acceptable carrier.

2. The method of claim 1 wherein the composition further comprises an organic sunscreen selected from the group consisting of Benzophenone-3, Benzophenone-4,Benzophenone-8,DEA, Methoxycinnamate, Ethyl dihydroxypropyl-PABA, Glyceryl PABA, Homosalate, Methyl anthranilate, Octocrylene, Octyl dimethyl PABA, Octyl methoxycinnamate (PARSOL MCX), Octyl salicylate, PABA, 2-Phenylbenzimidazole-5-sulphonic acid, TEA salicylate, 3-(4-methylbenzylidene)-camphor, Benzophenone-1,Benzophenone-2, Benzophenone-6,Benzophenone-12, 4-Isopropyl dibenzoyl methane, Butyl methoxy dibenzoyl methane (PARSOL 1789), Etocrylene, and mixtures thereof.

3. The method of claim 1 wherein the compound is present in an amount from about 0.1 wt. % to about 5 wt. %.

4. The method of claim 1 wherein the compound is 4-cyclopentyl methyl resorcinol, 4 cyclohexyl methyl resorcinol or a mixture thereof.

5. The method of claim 1 wherein the composition further comprises a skin benefit agent selected from the group consisting of alpha-hydroxy acids and esters, beta-hydroxy acids and esters, polyhydroxy acids and esters, kojic acid and esters, ferulic acid and ferulate derivatives, vanillic acid and esters, dioic acids and esters, retinol, retinal, retinyl esters, hydroquinone, t-butyi hydroquinone, mulberry extract, licorice extract, resorcinol derivatives, and mixtures thereof.

6. The method of claim 2 wherein the organic sunscreen is present in an amount of about 1 wt % to about 10 wt % of said composition; and
wherein the weight ratio of said organic sunscreen to said compound is about 10000:1 to about 1:10000.

7. The method of claim 5 wherein the skin benefit agent is selected from the group consisting of aipha-hydroxy acids, beta-hydroxy acids, polyhydroxy acids, hydroquinone, t-butyl hydroquinone, 4-substituted resorcinol derivatives, and mixtures thereof.

* * * * *